United States Patent [19]
Atlee, III

[11] Patent Number: 5,370,679
[45] Date of Patent: Dec. 6, 1994

[54] ESOPHAGEAL PROBE FOR TRANSESOPHAGEAL CARDIAC STIMULATION

[76] Inventor: John L. Atlee, III, N71 W29436 Tamron Ln., Hartland, Wis. 53029

[21] Appl. No.: 215,939

[22] Filed: Mar. 21, 1994

Related U.S. Application Data

[62] Division of Ser. No. 959,979, Oct. 13, 1992.

[51] Int. Cl.5 ............................................. A61N 1/05
[52] U.S. Cl. ................................... 607/124; 128/642
[58] Field of Search ............... 607/124, 119, 116, 133, 607/9; 128/642

[56] References Cited

U.S. PATENT DOCUMENTS 1,207,479 12/1916 Bisgaard .............................. 604/104
4,706,688 11/1987 Don Michael et al. ............. 128/642
5,170,803 12/1992 Hewson et al. ..................... 607/124

FOREIGN PATENT DOCUMENTS 2659240 9/1991 France ................................ 607/117

Primary Examiner—William E. Kamm
Assistant Examiner—Kennedy J. Schaetzle
Attorney, Agent, or Firm—Michael, Best & Friedrich

[57] ABSTRACT

An esophageal probe for transesophageal cardiac stimulation or monitoring. The probe comprises an elongate member adapted to be positioned within the esophagus of a patient and having a distal end and a proximal end. A second elongate member is slidably mounted on the first and engages at least one electrode carrier for selectively displacing an electrode laterally relative to the elongate member for positioning the electrode at the optimal position for cardiac stimulation and monitoring of the patient.

9 Claims, 2 Drawing Sheets

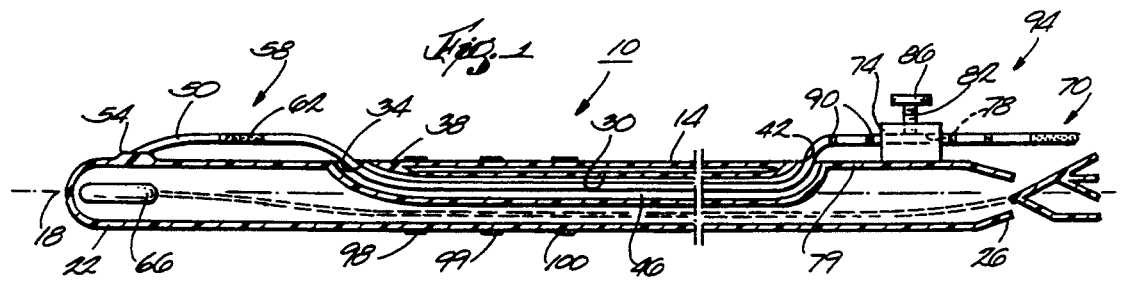

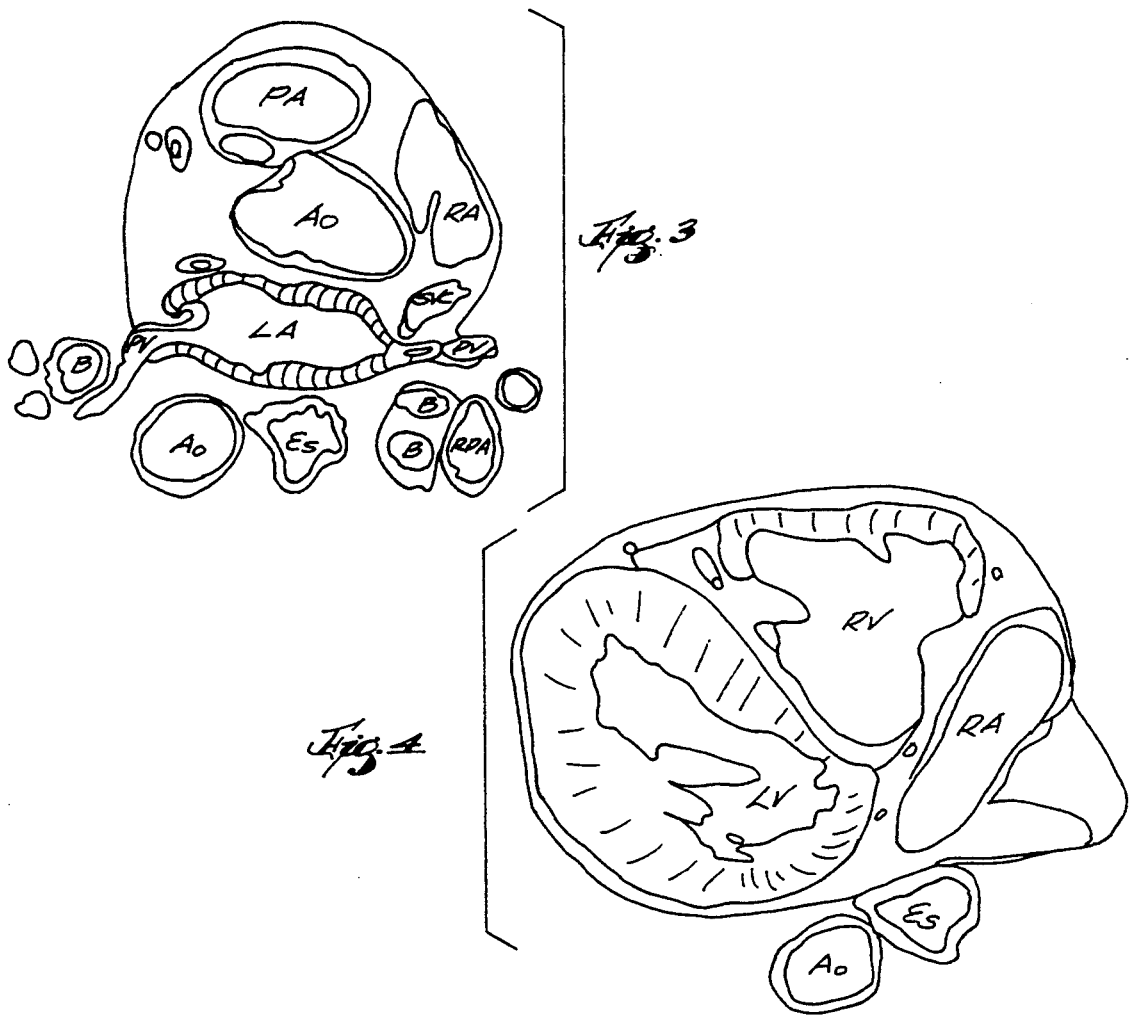
Fig. 3
Fig. 4
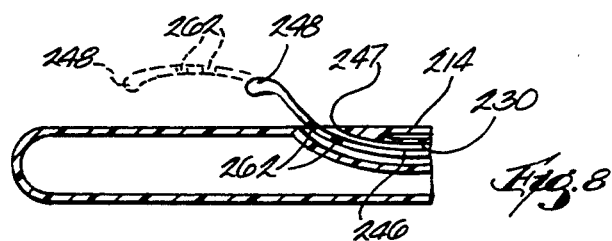
Fig. 8
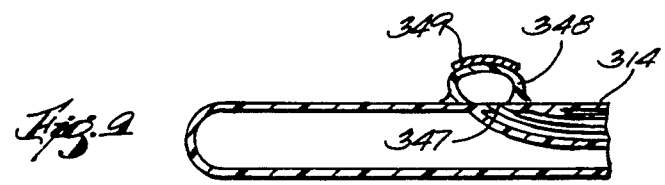
Fig. 9

ESOPHAGEAL PROBE FOR TRANSESOPHAGEAL CARDIAC STIMULATION

This is a division of co-pending application Ser. No. 07/959,979 filed Oct. 13, 1992, entitled "ESOPHAGEAL PROBE FOR TRANSESOPHAGEAL PACING"

BACKGROUND OF THE INVENTION

This invention relates to an esophageal probe and more particularly to a probe for transesophageal monitoring of cardiac activity and transesophageal stimulation of the heart, such as cardiac pacing or electroversion (cardioversion or defibrillation).

Transesophageal probes have been adapted for producing echo-cardiograms, measuring transesophageal ECG's, for use as transesophageal stethoscopes, and to achieve transesophageal cardiac monitoring, pacing and cardiac electroversion. It has been determined that transesophageal probe monitoring, pacing and electroversion can provide an attractive alternative to existing invasive (transvenous or epicardial) and non-invasive (transcutaneous) methods of cardiac stimulation.

It has been widely demonstrated that transesophageal atrial pacing (TAP) can be successfully performed in a substantial majority of anesthetized patients. However, TAP is not possible nor helpful in patients experiencing atrial fibrillation or complete A-V heart block. In these cases, temporary ventricular pacing is required to alleviate bradycardia occurring in combination with rhythm disturbances. For this reason, it would be desirable to perform indirect transesophageal ventricular pacing (TVP) as an alternative to the existing invasive (transvenous or epicardial) or non-invasive (transcutaneous) methods for cardiac stimulation. Unfortunately, the success rate of TVP capture using conventional and known transesophageal probes is much lower than the incidence of capture with TAP.

One attempt to solve the problem of TVP capture employs an esophageal probe having a stimulating electrode mounted on an inflatable balloon. When the electrode is deemed to be appropriately positioned in the esophagus and adjacent the posterior wall of the left ventricle, the balloon is inflated by means of an air supply conduit extending through the esophageal probe. Inflation of the balloon lodges the electrode in place in the esophagus. While this technique provides an increased incidence of TVP capture by reducing the esophageal-posterior left ventricular distance and providing adequate electrode contact, it has not been wholly satisfactory. If the balloon is over-inflated, or left in place for an extended period of time, the concentrated circumferential force of the balloon overpressure on the esophageal mucosa can cause damage to the tissue. In the alternative, if the balloon is not sufficiently inflated and the esophageal-posterior left ventricular distance is not adequately reduced, a higher energy stimulating pulse is necessary to achieve TVP capture. Under these circumstances, extended use of TVP with a pulse energy which is higher than ideal might also cause damage to the esophageal tissue. Each of these effects are undesirable, particularly in patients suffering from circulatory shock consequent to severe bradycardia.

An alternative to the balloon mounted electrode is to use a conventional esophageal stethoscope having surface mounted electrodes. However, because of the reduced contact between the electrode and the esophageal mucosa, and the increase in the distance between the esophagus and the posterior wall of the left ventricle, stimuli having higher current and longer pulse durations must be supplied to the electrode. Once again, this poses the risk of damage to the esophageal tissue.

Thus, it is desirable to provide an esophageal probe that can provide reliable TVP capture while reducing the risk of damaging the esophagus.

SUMMARY OF THE INVENTION

According to one aspect, the invention comprises an esophageal probe for transesophageal cardiac stimulation or monitoring comprising an elongate member constructed and arranged to be positioned within the esophagus of a patient and having a distal end and a proximal end, an electrode; and positioning means for selectively displacing the electrode laterally relative to the elongate member for positioning the electrode at the optimal position for cardiac stimulation and monitoring of the patient.

It is an object of the invention to provide a new and improved esophageal probe for transesophageal cardiac stimulation and monitoring.

A further object of the invention is to provide an esophageal probe for transesophageal cardiac stimulation and monitoring which does not damage the esophageal mucosa.

It is another object of the invention to provide a transesophageal probe for improved TVP capture by improving the electrode contact with the esophageal mucosa.

It a further object of the invention to provide an esophageal probe for improved TVP capture by reducing the esophageal-posterior left ventricular distance.

A still further object of the invention is to provide an esophageal probe for producing separate discrete atrial and ventricular stimulation.

Yet another object of the invention is to provide an esophageal probe for transesophageal cardiac stimulation wherein the stimulation threshold is reduced.

A further object of the invention is to provide a probe for transesophageal cardiac stimulation wherein the distance between the esophageal mucosa and the posterior left atrium or left ventricle is reduced.

It is a further object of the invention to provide a probe for transesophageal cardiac stimulation which permits indirect ventricular pacing.

These and further objects and advantages of the invention will become apparent from the detailed description thereof taken with the accompanying drawings.

BRIEF DESCRIPTION OF THE DRAWINGS

FIG. 1 is a side elevational view of the preferred embodiment of the invention;

FIG. 2 is a side elevational view of an alternate embodiment of the invention;

FIGS. 3 and 4 are cross sectional views through a portion of the human anatomy for illustrating the invention.

FIG. 5 is a side elevational view illustrating another embodiment of the invention;

FIG. 6 is a side elevational view illustrating another embodiment of the invention;

FIG. 7 is an end view of the esophageal probe illustrated in FIG. 4;

FIG. 8 is a side elevational view illustrating another embodiment of the invention; and FIG. 9 is a side elevational view illustrating another embodiment of the invention.

DETAILED DESCRIPTION OF THE PREFERRED EMBODIMENT

FIG. 1 illustrates an esophageal probe 10 according to the preferred embodiment of the invention for transesophageal cardiac stimulation and monitoring. The esophageal probe 10 includes an elongate member 14 that is semi-rigid and has a longitudinally extending axis 18. Ideally, the probe is similar to conventional esophageal stethoscopes in that it must be sufficiently rigid to allow insertion into the esophagus, but be sufficiently pliable to prevent damage to the tissue.

The elongate member 14 has a distal end 22, a proximal end 26, and a lumen 30 extending between the ends 22 and 26 and extending in general parallelism with the longitudinal axis 18 of the elongate member 14. The lumen 30 has a first exit opening 34 formed adjacent the distal end 22 of the elongate member 14. The interface of the lumen 30 and member 14 includes an annular seal 38 of medical grade silicon. The lumen 30 extends longitudinally within the elongate member 14 from exit opening 34 to a second exit opening 42 adjacent the proximal end 22 of the elongate member 14.

A flexible electrode catheter 46 is disposed partially within the lumen 30 and has a distal end 50 which is fixed to the elongate member 14 adjacent its distal end 22. The point of fixation between the catheter 46 and the elongate member 14, also includes a seal 54 of medical grade silicon. Between the distal end 22 and the lumen exit opening 34, the catheter is disposed outside the elongate member 14 to define a bowed portion 58.

The esophageal probe 10 includes at least one electrode 62 mounted on the bowed portion 58 of the catheter 46. While only one electrode is shown in FIG. 1, a plurality of electrodes may be required for cardiac pacing or monitoring or to achieve synchronous A-V stimulation. Furthermore, the probe may be adapted to accommodate additional transducers desired for the purpose of measuring select bio-physical parameters, i.e., a thermistor 66 to measure body temperature. Such a probe having plural electrodes 62a and 62b are shown in FIG. 2.

The probe 10 further includes positioning means for selectively displacing the electrode 62 axially relative to the elongate member 14 in order to position the electrode 62 at the optimum position for cardiac stimulation and monitoring. In part, the positioning means includes the bowed portion 58 of the flexible electrode catheter 46. The positioning means further includes a manipulating means including, an engageable section 70 at the proximal end 26 of the electrode catheter 46 and positioned externally of the exit opening 42 of the lumen 30. It will be appreciated that the engageable section 70 can be used to grip the flexible electrode catheter 46 and slide it axially along the lumen 30. Because the distal end 50 of the flexible electrode catheter 46 is fixed to the distal end 22 of the elongate member, the sliding of catheter 46 axially along the lumen 30 displaces the bowed portion 58 of the flexible catheter 46 relative to the axis 18. If the catheter 46 is moved toward the distal end 22, the bowed portion 58 displaces outwardly, further moving the electrode 62 laterally relative to the axis 18 and slightly toward the distal end 22 of the member 14. On the other hand, if the catheter 46 is forced proximally, the bowed portion 58 will be drawn inwardly and thereby move the electrode 62 toward the axis 18 of the elongate member 14 and a slight movement toward the proximal end 26. In either case, the electrode 62 mounted on the bowed portion 58 experiences both axial movement relative to the elongate member 14 as well as movement toward or away from the axis 18 of the elongate member 14.

The positioning means further includes means adjacent the proximal end 26 of the elongate member 14 for retaining the positioning means in a selected displaced position. In the preferred embodiment of the invention, the retaining means includes a collar 74 fixed to the elongate member 14 and defining a passage 78 for receiving the exposed proximal portion 79 of electrode catheter 46. The collar 74 further includes a threaded bore 82 communicating with the channel 78 and orientated generally perpendicular to the passage 78. A thumbscrew 86 is threadably received in the bore 82 for selective engagement with the catheter 46 to secure the catheter 46 in place along the channel 78 at any desired position of longitudinal adjustment. When the flexible catheter 46 is adjusted so that the electrode is in the optimal position for cardiac stimulation and monitoring, the thumbscrew 86 may be tightened into engagement with the flexible catheter 46, thereby securing the catheter in position relative to the elongate member 14 and retaining the contacts 62 in the selected optimal position. As long as the electrode catheter 46 is fixed, the displacement of the electrode 62 relative to the elongate member 14 remains constant to provide consistent contact with the esophageal mucosa (not shown). In addition, the pressure of the electrode will also decrease the distance between the esophageal wall (not shown) and the posterior wall of the left ventricle (also not shown).

The portion 79 of electrode catheter 46 also includes position marks 90 to allow easy notation of the position of the electrode catheter 46 so that when the optimal degree of bowing is determined for a particular patient, that position may later be recreated to facilitate quick placement of the electrode.

In the preferred embodiment, the probe 10 may also include one or more indifferent electrodes 98 located proximal to the electrode 62 on the bowed portion 58 and fixed to the elongate member 14. These electrodes 98, 99 and 100 may be used for monitoring various bio-physical parameters, as reference electrodes, in combination with electrode 62 for defibrillation or cardioversion, or referenced to a transcutaneous electrode on the patient's chest. Furthermore, it is possible that the electrodes 98-100 may be point electrodes, circumferential electrodes, oval or elliptical electrodes or otherwise. While any electrodes may be used, their configuration is critical only if the requirements of the particular application dictate. Their configuration is not critical to practice the invention.

The materials employed in the probe 10 must be biocompatible and non-biodegradable, and the surfaces must be non-abrasive and relatively soft or pliable so as not to pose the risk of esophageal mucosa abrasion or tears. The tip of the elongate member 14 must also be relatively soft and pliable so as not to cause esophageal perforation. The electrode catheter 46 can be of any suitable conductive material so long as it is biocompatible, non-corrosive, non-biodegradable, and sufficiently stiff to form and maintain the portion 58 bowed. All of the materials used in the probe 10 which are placed in the esophagus must be non-biodegradable for at least a period of several months, since this would otherwise affect its operation if used for extended periods of up to several days. In the preferred embodiment, the elongate member 14 is formed of polyvinylchloride.

In the preferred embodiment, the electrode catheter 46 is formed of a conductive stainless steel wire, which is relatively flexible, yet stiff enough to pass easily through the lumen 30. In addition, the electrode 62 and the indifferent electrodes 98, 99 and 100 are also preferably formed of stainless steel. Also in the preferred embodiment, the electrode 62 is located at the center point of the exposed bow portion when the probe is advanced 2 cm. from the proximal end and the electrode 62 is preferably positioned about 1–3 cm. laterally from elongate member 14 in order to produce approximation to the left atrium or ventricle. The center of the indifferent electrodes 98, 99 and 100 should be approximately 4, 6 and 8 cm., respectively, from the center of the electrode 62. When two or more electrodes 62a and 62b are located along the bow 50 as shown in FIG. 2, the inter-electrode spacing is preferably between 1.5 and 2 cm. Those skilled in the art will appreciate that any well known electrical insulating materials (now shown) is positioned between the electrodes 62 and the carrier 46.

FIGS. 3 and 4 are horizontal cross-sections of a male about 5'6" tall, 130 pounds, and 60–65 years of age and taken at about 130 mm. and 180 mm., respectively, below the fifth cervical vertebra. Those portions of the anatomy are identified in the drawings as follows:

Ao—Aorta
Es—Esophagus
LA—Left atrium
PV—Pulmonary vein
B—Bronchus
RPA—Right pulmonary artery
SVC—Superior vena cava
PA—Pulmonary artery
RA—Right atrium
LV—Left ventricle
RV—Right ventricle FIG. 3 shows that the esophagus is close to the left atrium at a point about 130 mm. below the reference noted above and that the left ventricle is close to the esophagus at 180 mm. below the reference. Therefore, for transesophageal pacing of the left atrium, the electrode in this particular individual should be positioned at 130 mm. and for pacing of the left ventricle, the electrode should be positioned about 50 mm. lower and offset through a horizontal angle of about 45 degrees from the most proximate point of the left ventricle shown in FIG. 3.

By extending the bowed portion 58 outwardly, the distance between the esophageal mucosa and the posterior left atrium as shown in FIG. 3 or left ventricle as shown in FIG. 4 can be reduced to 1 cm. or less. Also, by reducing the separation of the esophageal points for atrial and ventricular stimulation to about 5 cm. in this particular (representative) patient, separate atrial and ventricular stimulation can be obtained with the lowest stimulation thresholds. These stimulation points will be approximately 2 cm. above and below the atrioventricular (AV) groove, respectively, and within 1 cm. of the point where the maximal deflection atrial (Pwave-Pmax) or ventricular (Vwave-Vmax) depolarizations can be obtained (esophageal electrocardiogram (ECG)). Identification of Pmax and Vmax is a prerequisite to any attempt to locate the preferred points for indirect cardiac stimulation. Indirect ventricular stimulation is possible with a point electrode or anode at or within 1 cm. of Vmax referenced to a circumferential electrede or catheter approximately 5 to 7 cm. proximal. By using a bowed ventricular electrode, the esophageal mucosa ventricular distance can be reduced so as to accomplish indirect ventricular pacing in most, if not all, adult patients. The electrode according the preferred embodiment of the invention accomplishes reduced atrial- or ventricular-esophageal distance to about 1 cm. or less, while producing only localized and, therefore, dissipated pressure on the esophageal mucosa. This is critical with low perfusion states and cannot be accomplished by balloon electrodes in the esophagus.

If the probe according to the preferred embodiment of the invention is combined with an esophageal stethoscope, electrodes 62 should be located distal to the acoustic diaphragm by at least 4 cm. in adults and somewhat less in children to preserve acoustic function of the stethoscope. Probes may also be catheter or esophageal obturator devices for emergency or investigative procedures, such as stress, electrophysiologic study, pacing and cardiac electroversion by anesthesiology, cardiology, or emergency medical practitioners and use by paramedical personnel during cardiopulmonary resuscitation. Catheter probes can also be equipped with thermistor, obturator probes, and should be long enough for transnasal or transoral insertion. The probe may also include separate lumens for esophageal or gastric suctioning, the introduction of other sensors into the esophagus, the stomach or intestines and, when probes are used in conscious or sedated patients, a separate lumen may be provided for the introduction of topical anesthetics into the esophagus. The latter lumen would have an exit port at the level of the stimulating and recording electrodes.

FIG. 5 illustrates a probe 102 in accordance with an alternate embodiment of the invention. The probe 102 includes a transparent elongate tubular member 104 which is slidably mounted over a relatively rigid wire 106 having a proximal end 118, and a distal end 122. The wire 106 extends longitudinally through the tube 104 and projects from an exit opening 126 in the distal end 130 and a second exit opening (not shown) in the proximal end (not shown) of the member 104.

Fixed to the distal end of the tubular member 104 is a flexible electrode carrier 136 having a central leg 137 generally parallel to wire 106 and spaced therefrom, and a pair of legs 138 and 139, each integral at one end with leg 137 and fixed respectively at their opposite ends to the distal end 122 of wire 106 and the distal end 130 of tubular member 104. One or more electrodes 142 are mounted on leg 137 in a spaced apart relation to accommodate various applications. The proximal end 118 of the rigid tube 106 extends beyond the proximal exit opening 143 of tubular member 104. This extension permits the wire 106 to be displaced longitudinally relative to the tubular member 104. A suitable clamping device, such as thumb screw 144 and fixed nut 145 may be provided to secure the wire 106 in a fixed position relative to the tubular member 106. The opening 126 in the distal end of tube 104 is suitable sealed by a material, such as Teflon.

In operation, the degree to which the flexible electrode carrier 136 is bowed may be adjusted by sliding the wire 106 axially relative to the tubular member 104. Sliding the wire 106 toward the distal end of member 104 will cause the electrode carrier 136 to bow outwardly relative to the axis 146 of member 104. As the carrier 136 bows outwardly, the center leg 137 and its electrodes 142 will move laterally relative to the axis 146 and toward the distal end 130 of the tubular member 104. Alternatively, sliding the wire 106 toward the distal end of tubular member 104 will reduce the bow of carrier 136, thereby moving the center leg 137 and its electrodes 142 inwardly relative to the axis 146 and away from the distal end 130 of the tubular member 104.

A thumbscrew 162 may be provided to lock the wire 106 relative to the tubular member 104.

Preferably, either the wire 106 or the tubular member 104 includes gradations or markings such as 166 to provide a reference with which to note the position of adjustment of the carrier 136 relative to the wire 106. In the embodiment of FIG. 5, the gradations 166 are on wire 106 and are viewed through the transparent tubular member 104.

FIGS. 6 and 7 illustrate a probe 170 according to an alternate embodiment of the invention. The probe 170 includes a transparent, elongated tubular member 172 which is slidable mounted over a relatively rigid tube 174 having a proximal end 175 and a distal end 177. The tube 174 extends longitudinally through the tube 172 and out exit opening 178 and 179 in the distal and proximate ends of tube 172.

A pair of electrode carriers 180 and 182 are fixed longitudinally to the outer surface of tube 172 and in a spaced apart parallel relation one to the other. It will be appreciated that electrodes 180 and 182 are identical and, accordingly, only electrode 180 will be described in detail for the sake of brevity.

Electrode carrier 180 includes a first linear portion 184 fixed to the outer surface of tube 172 and a bowed electrode carrier 185 at its distal end. The electrode carrier 185 includes a center leg 187 extending generally in the axial direction and having one or more electrodes 188, 189 fixed thereto in a spaced apart relation. In addition, the electrode carrier 180 includes a first leg 191 extending from the central leg 187 to the linear portion 184 and a second leg 194 extending from the central leg 187 to the rigid tube 174, where it is fixed to the distal end 177 by a medical grade silicone seal. A clamping assembly 192 similar to that disclosed with respect to FIG. 5 is provided for fixing the rigid tube 174 relative to the tubular member 172.

For the individual whose cross-sections are illustrated in FIGS. 3 and 4, the electrode carriers 180 and 182 of the embodiment of FIGS. 6 and 7 are offset through an angle of about 45 degrees as shown in FIG. 7 and the center of electrede carrier 180 is about 5 cm. closer to the distal end than the electrode carrier 182. While it will be appreciated that this angle and distance will vary from individual to individual depending upon size, this angle and distance is typical, with the values for a range of individuals being about 40-50 degrees offset and a distance of 4-6 cm. Thus, in the event of a heart block, for example, when it is desirable to pace both the atrium and the ventricle, the probe such as that shown in FIG. 6 or 7 could be employed. Pacing pulses would then be applied in a proper sequence alternately and with an appropriate atrioventricular delay through the electrodes on carriers 180 and 182. Under other conditions, such as in the case of atrial fibrillation, pace signals to the ventricle alone would be necessary. In this case, the pace signal would be applied through the electrodes on carrier 182 alone or through an esophageal probe having a single electrode such as that shown in FIGS. 1, 2, 5 and 6, 7. In either case, the probe according to the invention having an extendable electrode bearing against the esophagus would reduce the distance between the esophagus and the left atrium or left ventricle, as the case may be. Based on preliminary investigations in man, it is believed that atrial pacing pulses should be about 15 mA or less and have a duration of about 10 milliseconds or less, while for ventricular pacing the pulse should be about 25 mA or less for durations of 15 milliseconds or less.

A further embodiment of the invention is shown in FIG. 8 wherein the probe includes an elongate member 214 similar to the tubular member 14 shown in FIG. 1. In particular, the member 214 includes a lumen 230 extending longitudinally therethrough for receiving a flexible electrode catheter 246 extending therethrough and from an exit opening 247 adjacent its distal end. The electrode 246 is not fixed at its distal end to the tube 214, but projects outwardly from the opening 247 at an oblique angle. In addition, the end of the electrode 246 has a soft tip 248 for engaging the esophagus. One or more electrodes 262 are mounted on the catheter 246 and in spaced apart relation adjacent the tip 248. In operation, the catheter 246 will be moved longitudinally relative to the tube 214 in the manner discussed with respect to FIG. 1. This will move the tip 248 outwardly and at an oblique angle for engagement with the wall of the esophagus, causing the tip 248 to flex, thereby bringing the electrodes 262 into pressure engagement with the esophageal tissue. A second identical electrode catheter (not shown) could be provided at an offset angle of 40°-50° and displaced 4-6 cm. toward the proximal end.

Another embodiment of the invention illustrated in FIG. 9 includes a tubular member 314 similar to the member 14 of FIG. 1. Affixed to the member 314 and over the exit opening 347 in its distal end is an inflatable "bleb" electrode carrier 348. One or more electrodes 349, formed of a material such as aluminum foil or conductive, painted surface, are fixed to the outer surface of the carrier 348. Inflation of the carrier 348 will move the "blab" electrode(s) 349 into contact with the esophageal mucosa.

It will be appreciated that each of the electrodes 62, 98, 99 and 100 of FIG. 1; 142 of FIG. 5; 188 and 189 of FIG. 6; 262 of FIG. 8; and 349 of FIG. 9 will each be connected by leads extending through the probe and to a terminal on its proximal end for connection by a lead (not shown) to the measuring or monitoring apparatus.

The esophageal probes illustrated in FIGS. 1,2 and 5-9 all satisfy the requirements for transesophageal indirect ventricular pacing. In particular, the electrode portions reliably reduce the esophageal luminal-to-posterior left ventricle or left atrium distance to 1 cm. or less. In addition, it permits this distance to be maintained regardless of changes in position of the heart or transthoracic pressure due to posturing, respiratory excursions, and positive pressure ventilation and the like. Moreover, the electrodes do not cause excessive pressure on the mucosa of the esophagus, which interferes with the blood supply to that tissue. While the electrodes may cause some localized pressure, this is dispersed in contrast to inflatable circumferential balloon electrodes, which might cause global overpressure. The optimum pacing, stimulation position can be recognized by the operator when a maximal amplitude ECG P-WAVE (Pmax-atrial position), or R/S wave (Vmax-ventricular position) is recorded from the respective electrodes.

Only a single electrode and carrier or catheter are shown in the embodiments of FIGS. 1, 2, 5, 8 and 9. However, those skilled in the art will appreciate that each may also include a second electrode and carrier displaced 4–6 cm. axially and at an angle of about 40°–50° as discussed with respect to the embodiment of FIGS. 6 and 7.

While only a few embodiments of the invention have been illustrated and described, it is not intended to be limited thereby, but only by the scope of the appended claims.

I claim:

1. A method of providing pace signals to a patient and including the steps of:
   positioning an elongate probe having a longitudinal axis in the patient's esophagus,
   positioning a first electrode on said probe at a location where the patient's esophagus is directly behind the left atrium,
   positioning a second electrode in said esophagus at a position where said esophagus is directly behind the patient's left ventricle at a rotational angle of about 40°–50° relative to said first electrode, and
   providing an electrical pulse through at least one of said electrodes.

2. The method set forth in claim 1 and including the step of biasing at least one electrode against the wall of the esophagus and displacing the wall of the esophagus toward the patient's heart for reducing the distance between said electrode and the patient's heart, the point of engagement between the electrode and the esophagus being localized.

3. An esophageal probe for transesophageal cardiac stimulation or monitoring, the probe comprising:
   an elongate member constructed and arranged to be positioned within the esophagus of a patient and having a distal end and a proximal end,
   first and second electrode carriers;
   first and second electrodes being mounted respectively on said first and second electrode carriers, said electrode carriers being positioned such that said first and second electrodes are spaced apart longitudinally and at different radial angles relative to an axial plane defined said elongate member;
   positioning means for selectively displacing said electrode carriers laterally relative to said elongate member for positioning said first electrode means at the optimal position for cardiac stimulation or monitoring of patient,
   said positioning means being at least partially resilient for resiliently urging said electrode means into pressure engagement with a patient's esophagus, 4. The esophageal probe set forth in claim 3 wherein said electrodes are spaced apart longitudinally about 4–6 cm, and at a radial angle of about 40°–50°.

5. The probe set forth in claim 3 wherein said axial distance is about 4–6 cm. and the rotational displacement between said electrodes being 40°50°.

6. The probe set forth in claim 5 wherein said positioning means includes resilient means for separately supporting each of said electrode means, said positioning means being operative to resiliently bias said first and second electrode means into engagement with the esophageal mucosa for moving the same into closer proximity with the atrium or ventricle of a patient's heart.

7. An esophageal probe for transesophageal cardiac stimulation or monitoring, the probe comprising:
   an elongate member having a longitudinal axis and being constructed and arranged to be positioned within the esophagus of a patient and having a distal end and a proximal end,
   first and second electrode means spaced apart axially on said elongate member and being positioned at different rotational angles relative to said axis,
   positioning means for selectively displacing said electrode first and second electrode means laterally relative to said elongate member for positioning said first and second electrode means at the optimal position for cardiac stimulation or monitoring of the patient.

8. An esophageal probe for transesophageal cardiac stimulation or monitoring, the probe comprising:
   an elongate member constructed and arranged to be positioned within the esophagus of the patient and having a distal end and a proximal end,
   first and second electrode means,
   said elongate member having a longitudinal axis, said first and second electrodes being mounted on said elongate member in an axially spaced apart relation and being positioned at different rotational angles relative to an axial plane defined by said axis.

9. The probe set forth in claim 8 wherein the axial distance between said electrodes is about 4–6 cm. and the rotational displacement between said electrodes being 40°–50°.

* * * * *